United States Patent [19] | [11] Patent Number: 5,089,386
Stackebrandt et al. | [45] Date of Patent: Feb. 18, 1992

[54] TEST FOR LISTERIA

[75] Inventors: Erko Stackebrandt, Daenischenhagen, Fed. Rep. of Germany; Michael Curiale, Homewood, Ill.

[73] Assignee: Gene-Trak Systems, Framingham, Mass.

[21] Appl. No.: 96,510

[22] Filed: Sep. 11, 1987

[51] Int. Cl.$^5$ ............................................. C12Q 1/68
[52] U.S. Cl. ......................................... 435/6; 435/30; 435/34; 435/35; 435/36; 435/38; 435/822; 436/175; 436/501; 536/27; 935/3; 935/19; 935/20; 935/78; 935/86
[58] Field of Search .................... 435/6, 30, 34, 35, 36, 435/38, 822; 436/501, 175; 536/27; 935/3, 20, 19, 78, 86

[56] References Cited

U.S. PATENT DOCUMENTS

| | | | |
|---|---|---|---|
| 3,755,086 | 8/1973 | Heimer | 195/103.5 R |
| 4,139,346 | 2/1979 | Rabbani | 422/56 |
| 4,228,238 | 10/1980 | Swanson | 435/32 |
| 4,302,204 | 11/1981 | Wahl et al. | 23/230.3 |
| 4,358,535 | 11/1982 | Falkow et al. | 435/5 |
| 4,359,535 | 11/1982 | Pieczenik | 435/317 |
| 4,486,539 | 12/1984 | Ranki et al. | 436/504 |
| 4,717,653 | 1/1988 | Webster, Jr. | 435/5 |
| 4,851,330 | 7/1989 | Kohne | 435/6 |

FOREIGN PATENT DOCUMENTS

| | | |
|---|---|---|
| 0133671 | 3/1985 | European Pat. Off. |
| 0146039 | 6/1985 | European Pat. Off. |
| 2139349 | 11/1984 | United Kingdom |
| 8402721 | 7/1984 | World Int. Prop. O. |

OTHER PUBLICATIONS

Klinger et al. (1988) J. Assoc. OFF. Anal. Chem., vol. 71, No. 3, pp. 669-673.
Rocourt et al. (1987) Int. J. of Sys. Bact., vol. 37, No. 3, pp. 266-270.
Rocourt et al. (1987) Int. J. of Sys. Bact., vol. 37, No. 3, pp. 298-300.
Ludwig et al., (1984) FEMS Microbiology Letters, vol. 25, pp. 199-204.
Kennell, "Principles and Practices of Nucleic Acid Hybridization," Progress in Nuc. Acid Res. and Mol. Biol., 11: 259-301 (1971).
Cady et al., "Electrical Impedance Measurements: Rapid Method for Detecting and Monitoring Microorganisms," J. Clin. Microbiol., 7:265-271 (1978).
Fox et al., "The Phylogeny of Prokaryotes," Science, 209: 457-463 (1980).
Thomason, "Current Status of Immunofluorescent Methodology for Salmonellae," J. of Food Protection, 44: 381-384 (1981).
Woese, "Archaebacteria," Scientific American, 244: 98-122 (1981).
Gnan et al., "Impedance Measurements in Raw Milk as an Alternative to the Standard Plate Count," J. of Food Protection, 45: 4-7 91982).
Langer et al., "Enzymatic Synthesis of Biotin-Labeled Polynucleotides: Novel Nucleic Acid Affinity Probes," Proc. Natl. Acad. Sci., 78: 6633-6637 (1981).
Goor et al.1, "Taxonomic localization, by DNA:rRNA hybridization, of unclassified phytopathogenic Pseudomonas species", Antonie van leeuwenhock 50: 302-303 (1984).
Fitts et al., "DNA-DNA Hybridization Assay for Detection of Salmonella spp. in Foods", Applied and Environ. Microbiol., 46: 1146-1151 (1982).
Fitts, "Development of a DNA-DNA Hybridization Test for the Presence of Salmonella in Foods," Food Technology, 39: 95-108 (1985).

*Primary Examiner*—Amelia Burgess Yarbrough
*Assistant Examiner*—Ardin H. Marschel
*Attorney, Agent, or Firm*—Fish & Richardson

[57] ABSTRACT

Nucleic acid fragment capable of hybridizing to rRNA of *Listeria monocytogenes* and not to rRNA of *Bacillus subtilis*.

13 Claims, 1 Drawing Sheet

```
                        :------IG 563----------:
    L. monocytogenes    AAGCGCGCGCAGGCGGUCUUUUAA
    B. subtilis         ---G--U----------U--C---
    Brochothrix         --------------------C---
    Proteus vulgaris    ------A---------- -AA----
    E. coli             ------A----------U-G----
    Halobacterium       -----UC--U--C---C-ACGA-G :-----------IG 565-------------------:
    L. mon   UCGGAUUGUAGGCUGCAACUCGCCUGCAUGAAGCCGGAA
    B.S.     ------C-C--U----------A----G------U----
    B.T.     --------C---------------N--------------
    P.V.     C-------G--U----------A--C-------U-----
    E.C.     C-------G--U----------A--C-------U-----
    H.V.     --------AG-----A--------CU--------U---U :------------662----------------:
           :--------------661-------------:
           :-------564----------::-------566---------:
    L. mon UUACAUCCUUUGACCACUCUGGAGACAGAGCUUUCCCUUCGGGGACAAAGU
    L. inn -------------------------------------------------- 
    L. mur --------------------------------------------------
    B.S.   ---C----A-UC--A----U--GA-G-C----------G--G---
    B.T.   ----------U-----------A--G- ----------------
    P.V.   --AGC--AUC--U-A----U----GAG-G--------A--GCU-A
    E.C.   --ACG--AGUU-UCA----UGAGAA-G-G--------A--CGU-A
    H.V.   A-AG---UG--GA-C --GUU-- -GA--U-AUCAC---GCU--

:------663 complement 568----:
                                          :----------610------:
           :---------568----------------::--------------567--------------:
    L. mon UGGAUAGUACAAAGGGUCGCGAAGCCGCGAGGUGGAGCUAA UCCCAUAAAACUAUUCUCAG
    L. inn ----G-----------------------N----C-- -----------C---------
    L. mur ----GA---------N-----------------N------ -----------U---------
    B.S.   ---C--A--------CA------A----------UA---C--U-----C---U--G-------
    B.T.   -----A---------U-----------------N----C-- -----------U---------
    P.V.   --CAGA--------A-AA----CCU------AGCA---GG- A-U------GUCUG--GU--
    E.C.   --CGCA--------A-AA----CCU------AGCA---GG- C-U------GUGCG--GU--
    H.V.   --UCGAG----U----U--U-UCU--AA--AGAAC----- --U-C----CUCGA--GU--

:----------609------------------:
    L. mon      CCGAAGUCGGUAGGGUCACCUUUAUGGAGCCAGCCGC
    L. inn      ----------------N-------------
    L. mur      ----------------A------------------U--
    B.S.        -----------GA----UA-----------
    B.T.        --A---C----UU---A--- --CG-----U-----U
    P.V.        AA------A-----CU-A-----
    E.C.        AA------A-----CU-A-----
```

TEST FOR LISTERIA

BACKGROUND OF THE INVENTION

This invention relates to detecting bacteria belonging to the genus Listeria. (The term "Listeria," as used herein, refers to the bacteria classified as such in Bergey's Manual of Systematic Bacteriology, with the exception of *L. denitrificans,* which recently has been removed from the genus Listeria based on molecular and phenotypic consideration (Rocourt et al. (1987) International Journal of Systematic Bacteriology (submitted)). Detection of Listeria bacteria is important in various medical and public health contexts. Listeria infection can cause a variety of symptoms ranging from cold like to flu-like, but is especially dangerous for a fetus, where it induces a 50% mortality rate.

According to a standard laboratory method and a method recommended by the F.D.A., the presence of Listeria in environmental or dairy specimens (e.g., milk) is detected by culturing an appropriately prepared sample on microbiological media under conditions favorable for growth of these organisms. The resulting colonies are examined for morphological and biochemical characteristics, a process that typically is started 48 hours after acquisition of the sample and takes between 9-19 days to complete.

Kohne et al. (1968) Biophysical Journal 8:1104-1118 discuss one method for preparing probes to rRNA sequences.

Pace and Campbell (1971) Journal of Bacteriology 107:543-547 discuss the homology of ribosomal ribonucleic acids from diverse bacterial species and a hybridization method for quantitating these homology levels.

Sogin, Sogin, and Woese (1972) Journal of Molecular Evolution 1:173-184) discuss the theoretical and practical aspects of using primary structural characterization of different ribosomal RNA molecules for evaluating phylogenetic relationships.

Fox, Pechman, and Woese (1977) International Journal of Systematic Bacteriology 27:44-57 discuss the comparative cataloging (of 16S ribosomal RNAs) approach to prokaryotic systematics.

The present invention will be better understood in light of the following definitions:

DNA—deoxyribonucleic acid, the type of nucleic acid containing deoxyribose as the sugar component.

RNA—ribonucleic acid, the type of nucleic acid containing ribose as the sugar component and which, most generally, is transcribed (copied) from DNA. RNA molecules may serve informational (e.g., messenger RNA), catalytic, or structural (e.g., ribosomal RNA, see below) cellular functions.

rRNA—Ribosomal RNA (rRNA) molecules are key elements of ribosomes, complex protein and RNA-containing "organelles" which, together with transfer RNAs, comprise the translation apparatus. Ribosomes are of profound importance to all organisms because they serve as the only known means of translating genetic information into cellular proteins, the main structural and catalytic elements of life.

Ribosomes contain three distinct RNA molecules which, in *E. coli,* are referred to as 5S, 16S and 23S rRNAs. These names historically are related to the size of the RNA molecules, as determined by sedimentation rate. However, they actually vary substantially in size between organisms. 5S, 16S, and 23S rRNA are commonly used as generic names for the homologous RNA molecules in any bacteria, and will be so used here.

Hybridization—the process by which, under defined reaction conditions, two partially or completely complementary nucleic acids are allowed to come together in an antiparallel fashion and form specific and stable hydrogen bonds. The stringency of a particular set of hybridization conditions is defined by the base composition of the probe/target duplex, as well as by the level and geometry of mispairing between the two nucleic acids. Stringency may also be governed by such reaction parameters as the concentration and type of ionic species present in the hybridization solution, the types and concentrations of denaturing agents present, and/or the temperature of hybridization.

Probe(s)—synthetic or biologically produced nucleic acids (DNA or RNA) which, by design or selection, contain specific nucleotide sequences that allow them to hybridize, under defined stringencies, specifically (i.e., preferentially) to target nucleic acid sequences.

Target—a nucleic acid sequence to which a particular probe is capable of preferentially hybridizing.

Other definitions are given as their first use arises in the text.

SUMMARY OF THE INVENTION

The present invention features nucleic acid probes or probe sets consisting essentially of DNA or RNA sequences which are capable, under specific hybridizing conditions, of detecting the presence of ribosomal RNA (rRNA) molecules of *Listeria monocytogenes* and are not capable, under the same conditions, of detecting the rRNA of closely related *B. subtilis* bacteria which may be present in the test sample.

The present invention also features an assay system for the utilization of these probes, the format of which can enhance the aforementioned desirable behavior of the probes. The invention exhibits the following enhanced performance capabilities:

a) increased sensitivity; i.e., the ability to detect Listeria in a given sample more frequently than currently available methods, b) potentially significant cost reductions in probe production due to the use of chemically, rather than biologically, synthesized probes, c) accurate identification of even biochemically unusual Listeria, because of the rRNA sequence characterizations which provide the basis of such identification, and d) faster results because the test is performed on cultured cells which need not be grown further, the test of this invention taking only 2-4 days to provide a result.

The use of Listeria rRNA as target molecules provides a number of advantages, among them:

1) The rRNAs constitute a significant component of cellular mass. Although estimates of cellular ribosome content vary, actively growing Listeria bacteria may contain upwards of $5.0 \times 10^4$ ribosomes per cell, and therefore $5.0 \times 10^4$ copies of each of the rRNAs (present in a 1:1:1 stoichiometry in ribosomes). In contrast, most other potential cellular target molecules, genes or RNA transcripts thereof, are present in much lower abundance.

(2) The rRNAs (and the genes encoding them) appear not to be subject to lateral transfer between contemporary organisms. Thus, rRNA primary structure provides an organism-specific molecular target, rather than a gene-specific target as would likely be the case, for example, of a plasmid borne gene or product thereof which may be subject to lateral transmission between contemporary organisms.

In addition to providing the advantages inherent in rRNA detection, the present invention provides probes to Listeria rRNA target sequences which are sufficiently similar in a significant number of Listeria that one or a few probes can hybridize to the target region in those Listeria, and are sufficiently different in most non-Listeria rRNAs that, under some conditions where the probe(s) hybridize to Listeria rRNAs, they are not capable of hybridizing, or hybridize very poorly, to most non-Listeria rRNAs. These probe characteristics are defined as inclusivity and exclusivity, respectively. In addition, the probes of the invention hybridize to target regions which can be rendered accessible to the probes under normal assay conditions.

In a particularly preferred embodiment of the invention, an assay method is used in which bacteria in the sample are grown under conditions which allow rapid growth of any Listeria in the sample, but not of closely related Brochothrix species. Hybridization analysis is then performed on the sample after this growth period. In such an assay, some cross-hybridization of the probe with rRNA of the related Brochothrix bacteria can be tolerated because of the pre-hybridization selective amplification of the Listeria.

In another preferred embodiment, the Listeria detection method includes, prior to contacting the Listeria rRNA with one or more probes, the steps of subjecting the sample to a primary enrichment step for Listeria bacteria, followed by a secondary, non-specific bacterial enrichment step which is carried out in a buffer (most preferably, a 3-[N-Morpholino] propanesulfonic acid—containing buffer) to maintain the pH of the enriched sample between 6.5 and 8.0, most preferably about 7.2. This pH control, it has been found, permits the Listeria in the sample to grow much faster, during secondary enrichment, than is otherwise possible.

In another preferred embodiment, the Listeria detection method includes the step, prior to contacting the Listeria rRNA with one or more probes, of contacting the Listeria in the sample with an enzyme which weakens the Listeria bacterial cell walls, prior to subjecting the bacteria to lysis using a lytic agent, e.g., quanidinium thiocyanate. It has been found that this enzyme treatment greatly improves the hybridizaiton reaction.

Other features and advantages of the invention will be apparent from the following description of the preferred embodiments thereof, and from the claims.

Description of the Preferred Embodiments

Preferred embodiments of the invention are now described.

DRAWING

The Figure is the nucleotide sequence of five regions of Listeria 16S rRNA where Listeria/B. subtilis differences, shown, were discovered; corresponding rRNA sequences of B. subtilis, and other bacteria, are shown below Listeria sequences. L. mon represents L. monocytogenes (the Listeria species of greatest medical concern), L. inn represents L. innocua, L. mur represents L. murrayi, B.S. represents Bacillus subtilis, B.T. represents Brochothrix thermosphactum, P.V. represents Proteus vulgaris, E.C. represents E. coli, and H.V. represents Halobacterium volcanii.

PROBE DEVELOPMENT STRATEGY

The first step in the development of probes of the invention is to identify regions of 16S and 23S rRNA which potentially can serve as target sites for Listeria-specific nucleic acid probes. As a practical matter, it is difficult to predict, a priori, which non-Listeria organisms might be present in any test sample. Because of the large number of such potential non-Listeria bacteria, demonstrating exclusivity for any given probe sequence is extremely difficult and laborious. However, a more rigorous criterion can be adopted which obviates the need to know, during initial stages of research and development, what non-Listeria bacteria might be present in all test samples that ultimately will be screened using the probe. This entails a knowledge of the phylogenetic relationships among Listeria and between Listeria and other groups of bacteria. Specifically, it is taken as an operating hypothesis that the exclusivity criterion may be satisfied by determining that a particular target region in Listeria rRNA is sufficiently different from the homologous region in the rRNA of representative close evolutionary relatives of Listeria (in particular, B. subtilis) that the Listeria and relatives can be distinguished by hybridization using a probe specific to the Listeria seguence As a general rule then, based on phylogenetic principles, the rRNA seguences of more distantly related organisms, even though their actual identity is not necessarily known, can be predicted to be at least as different, in a particular region of seguence, than the aforementioned close evolutionary relative of Listeria, B subtilis.

As our first step in identifying regions of Listeria rRNA which might be useful as target sites for nucleic acid hybridization probes, we have determined nearly complete nucleotide sequences of the 16S rRNAs from three species of Listeria: L. monocytogenes, L.innocua, and L. murrayi. These were selected as representatives of the major Listeria DNA homology groups, and thus are representative of the evolutionary breadth of genus Listeria. Nucleotide seguences of various portions of the rRNAs were determined by standard laboratory protocols either by cloning (Maniatis et al. (1982) Molecular Cloning: A laboratory manual. New York: Cold Spring Harbor Laboratory, 545 pp.) and sequencing (Maxam et al. (1977) Proceedings of the National Academy of Science, U.S.A. 74:560–564; Sanger et al. (1977) Proceedings of the National Academy of Science, U.S.A. 74:5463–5467) the genes which specify the rRNAs, and/or by direct sequencing of the rRNAs themselves using reverse transcriptase (Lane et al. (1985) Proceedings of the National Academy of Science, U.S.A. 82:6955–6959).

These nucleotide sequences were compared to one another and to other available rRNA nucleotide sequences, in particular, to those of the closely related soil bacterium Bacillus subtilis. A number of regions were discovered that exhibit potentially useful exclusivity charcteristics with respect to the B. subtilis rRNA sequences (i.e., contain Listeria-specific sequences). Certain of these are shown in the Figure, and discussed below.

As discussed above, this preliminary analysis provides only a demonstration of feasibility. Further experimental testing of each nucleic acid probe is required to rigorously demonstrate the desirable characteristics discussed above, namely: 1) adequate exclusivity as to most or all closely related organisms, 2) useful inclusivity patterns with respect to Listeria, and 3) accessibility of the target regions under various assay conditions that might actually be employed. Because of the extremely large number of organisms potentially relevant to defining exclusivity and inclusivity characteristics of test probes, we have adopted the herein described interactive strategy with respect to testing and refinement of potential probes.

The first generation probes are designed based on the principle of maximizing utilization of the observed nucleotide sequence variation in the target regions of Listeria and non-Listeria bacteria. There is then carried out preliminary testing of the inclusivity and exclusivity properties of the first generation probes (which are synthesized by standard oligonucleotide techniques) by "dot blot" analysis. Dot blot analysis can be performed in many different ways, but generally involves immobilizing a nucleic acid or a population of nucleic acids on a filter (e.g., nitrocellulose, nylon, or other derivatized membranes which are commercially available and useful for this purpose). RNA can easily be so immobilized and then probed under any of a variety of nucleic acid hybridization conditions (i.e., stringencies), for nucleotide sequences of interest. Techniques are also available in which RNA present in crude (unpurified) cell lysates can be immobilized without having to first purify the nucleic acid in question. This latter approach significantly decreases the amount of effort required to screen for particular nucleotide sequences which may be present in the nucleic acids of any particular organism and, moreover, is amenable to the mass screening of large numbers of organisms. It, therefore, is the method of choice for testing the exclusivity and inclusivity properties of potential nucleic acid hybridization probes versus large numbers of organisms.

A list of non-Listeria bacteria which exemplify the type of bacteria that may be present in potentially Listeria containing samples is given in Table 1. These also represent many of the genera most closely related to Listeria. As discussed above, a probe which demonstrates good exclusivity characteristics to such a broad representation of bacteria can reasonably be predicted to behave similarly to a much broader list of organisms than actually tested. DNA probes 568, 609, and 661 (Figure) did not hybridize to over 90% of these bacteria, under the stringency conditions described in the Example, below. (Probes 568, 609, and 661, and the other probes of the Figure, are complementary (5' probe end to 3' RNA end) to the given L. monocytogenes rRNA sequences, i.e., the probes each have a C for the RNA's G, a T for the RNA's A, an A for the RNA's U, and a G for the RNA's C.)

Table 1

Partial Listing of Non-Listeria Bacteria Used in Screening Potential Probes

*Aeromonas sobria*
*Bacillus cereus*
*Bacillus subtilis*
*Brochothrix thermosphacta*
*Citrobacter freundii*
*Corynebacterium xerosis*
*Corynebacterium diptheriae*
*Escerichia vulneris*
*Enterobacter agglomerans*
*Enterobacter cloacae*
*Klebsiella pneumoniae*
*Klebsilla oxytoca*
*Lactobacillus casei*
*Pseudomonas aeruginosa*
*Rhodococcus equii*
*Salmonella arizonae*
*Salmonella cholerae-suis*
*Salmonella typhi*
*Serratia odorifera*
*Shigella boydii*
*Shigella flexneri*
*Shigella sonnei*
*Staphylococcus aureus*
*Staphylococcus epidermidis*
*Staphylococcus hominis*
*Staphylococcus saprophyticus*
*Streptococcus agalacticae*
*Streptococcus bovis*
*Streptococcus faecalis*
*Streptococcus faecium*
*Streptococcus lactis*
*Streptococcus mutans*
*Streptococcus pneumoniae*
*Streptomyces globisporus*
*Yersinia enterocolitica*

Probes 568, 609, and 661 (Figure) also exhibited good inclusivity properties, by binding. under the stringency conditions of the Example, to *L. monocytogenes, L. innocua, L. murrayi, L. ivanovii, L. seeligeri, L. welshimeri,* and *L. grayi.*

Several other considerations also affect optimal design characteristics of a probe sequence. The first is consideration of the geometry of the probe with respect to itself (i.e., intramolecular interactions). Potentially useful target regions of the 16S rRNA of *L. monocytogenes* may be located in regions that exhibit substantial potential for self complementarity. Therefore, probes to these regions can also exhibit self complementarity. Because potential interactions between the probe and target sequences are governed by the same types of interactions that govern the intramolecular annealing of the target or probe sequences to themselves, it is possible, particularly under solution hybridization conditions, that self-complementary probes can render themselves inaccessible for hybridization to their target sequences. Thus, one aspect of probe design is to minimize such self-complementarity. This can necessitate making a compromise between maximum utilization of Listeria-specific sequences and acceptable probe geometry.

An additional consideration in probe design arises with respect to the inclusivity criterion. Preferred probes are those which, while displaying appropriate exclusivity behavior, also can hybridize to the rRNA(s) of all desired Listeria bacteria. Because the genus Listeria itself is comprised of bacteria which exhibit significant phenotypic and genetic variations, it may not be possible to design (or discover) such an "ideal" probe. In practice, rather than demanding a "universal" Listeria probe, a set of Listeria-specific probes is sought, each of which exhibits appropriate exclusivity, and some useful level of inclusivity. In aggregate, the set of probes will detect most or all Listeria and few or no non-Listeria bacteria. In such a set, for example, one probe can detect all but one or a few important Listeria strains, and another probe may hybridize with good exclusivity only to those few Listeria strains missed by the first probe. Thus, although the probes disclosed below are characterized on an individual basis with respect to inclusivity characteristics, it must be borne in mind that the concept of "sets" of specific probes detailed above must also be considered in determining the importance of individual probes.

This set notion also extends to evaluation of the exclusivity behavior of individual probes. For example, in the detection format described below, undesirable hybridization to non Listeria bacteria by otherwise useful probes or probe sets can be reduced or abolished by manipulation of the assay strategy employed.

In some cases, it is preferred to have probes specific for just one species of Listeria, specifically *L. monocytogenes*, which is pathogenic to animals and especially to humans. Such probes are useful since they will not produce false positive results when non-pathogenic Listeria are in a sample, and thus a positive result indicates the presence of pathogenic Listeria.

The final step of probe design and analysis is testing of real (e.g., food/clinical) samples.

PROBES

The probe selection strategy described above has yielded a number of probes useful in identifying Listeria bacteria in samples. The first step in the probe selection process was to carry out nucleotide sequence analysis on the 16S rRNA of the three Listeria spp. listed above. Comparison of these Listeria sequences to non-Listeria rRNA sequences (particularly *B. subtilis* sequences) identified sequences which meet the exclusivity criterion, i.e., they are essentially Listeria specific, and are thus potential target regions to which probes could be directed. These regions are indicated in the Figure.

Liquid hybridization assays using probes 568 and 661 (the sequences of these probes are 568: 5' TCGCGGCTTCGCGACCTTTGTACTATCCA 3' and 661: 5' GGGAAAGCTCTGTCT-CCAGAGTGGTCAAAGG 3') demonstrate good accessability of target sequences in these regions under different hybridization conditions. Generally, good sensitivity also is achieved. However, these probes will hybridize under the above conditions to Brochothrix, and thus these bacteria must be selected against during the assay procedure. One method is to culture bacteria within a sample under conditions which do not allow Brochothrix to grow, e.g., at temperatures above 30° C., such as 32° C. or 35° C. In this way, false positive results are avoided because Brochothrix background is very low.

Probe 609 does not hybridize under the above conditions to Brochothrix and thus selective Listeria amplification is not needed where this probe is used as the only probe.

Probes specific to Listeria 23S rRNA can be derived as described above in the case of 16S rRNA.

The probes of the invention can be used in a variety of formats, one of which is described below.

EXAMPLE

The DNA hybridization test employs Listeria specific DNA probes labelled with a radioisotope (phosphorus-32, although other labels are equally suitable, e.g., fluorescent or chemiluminescent labels) to detect Listeria spp. in meat, dairy products and environmental samples following broth culture enrichment. After enrichment, bacteria present in the test samples are collected on membrane filters by vacuum filtration. The bacteria are lysed and the released nucleic acids are fixed to the membrane filters. Following a short prehybridization step, the filters are incubated in a hybridization solution to which the $^{32}$P-labelled Listeria-specific DNA probes are added. If Listeria nucleic acids (ribosomal RNA) are present in a test sample, the radiolabelled DNA probes will hybridize to the target nucleic acid sequences present on the filter. Unbound probe is washed away and the radioactivity on the filters is measured by counting in a scintillation counter or other beta particle detector. Radioactivity on a filter above a threshold value, determined by results obtained for negative control assays, indicates the presence of Listeria in the test sample. The assay is a qualitative test to determine the presence of Listeria spp. in dairy or meat products and environmental samples. A sample is considered non reactive for the presence of Listeria spp. if the counts per minute (cpm) value does not exceed the established cutoff value for the assay. A sample is considered reactive for the presence of Listeria spp. if the cpm value is greater than the established cutoff value for the assay.

The first step was primary enrichment for Listeria in the sample. For dairy product samples, 25 g of food sample was added to 225 ml of Listeria Enrichment Broth (EB; Trypticase soy broth powder 30 g, Yeast extract 6 g, Distilled water 1 liter, Acriflavin HCl 15 mg/liter, Nalidixic acid (Na salt) 40 mg/liter, and Cycloheximide 50 mg/liter.) The mixture was homogenized using a blender or stomacher as appropriate for the particular sample type, and then incubated in a flask or bottle for 24±4 hours at between 30° C. and 50° C., preferably 35° C.

For environmental testing, a swab or other environmental sample was placed in a flask or bottle containing 25 ml (or larger volume if required) EB, and incubated for 24±4 hours at between 30°-50° C., preferably 35° C.

The next step was secondary enrichment for all sample types. The primary enrichment culture was removed from incubation and mixed well. 1 ml of the primary enrichment culture was transferred to a flask or bottle containing 100ml modified Listeria Enrichment Broth (MEB; Trypticase soy broth powder 30g, Yeast extract 6 g, 3-[N-Morpholino] propanesulfonic acid-free acid (MOPS-free acid) 8.5 g, 3-[N-Morpholino] propanesulfonic acid-Na salt 8.5 g, (MOPS-vp Na salt) 13.7 g, Distilled water 1 liter, Acriflavin HCl 15 mg/liter, Nalidixic acid (Na salt) 40 mg/liter, and Cycloheximide 50 mg/liter) and incubated for 24±4 hours at 30°-50° C., preferably 35° C.

The following assay procedure makes use of the GENE-TRAK manifold kit (GENE-TRAK Systems Cat. No. GT801). One ml of the cultured cells were treated with 0.5 ml of enzyme solution (containing 3000 units of mutanolysin (available from Sigma) and 150 mg of lysozyme (available from Sigma) in 15 ml of 10xTE (-Hcl 1 mM, 7.6) buffer by incubation at room temperature (15°-30° C) for 15 min. The contents of each tube were then vacuum filtered into a filter cup. This results in a concentration on the filter of the cultured cells, the cell walls of which have been weakened by the enzymes.

The nucleic acid in these cells was then denatured as follows. Listeria lysing and denaturing solution (0.675M quanidine thiocyanate, 1xTE) was squirted into the filter cups until the filter was covered with liquid and after 2 minutes the solution vacuum filtered. Listeria neutralizing solution (1M Tris-Hcl pH 8, 0.6 M NaCl)

was then squirted into the filter cup until the filter was covered with liguid, and again after 2 minutes the solution was vacuum filtered. A Listeria fixation solution (95% ethanol, 5% water) was then squirted into the filter cup until the filter was covered with liguid and after 2 minutes the solution vacuum filtered.

The denatured nucleic acid on the filter was then hybridized, as follows. The filters were removed from the cups and placed in a 50 ml conical bottom tube containing 25 ml of Listeria prehybridization solution (6xSSC, 0.5%SDS, 1x Denhardts, 1 mM EDTA) prewarmed to 65° C. The tube and contents were placed in a 65° C. water bath for 30 minutes. The liquid was poured out of the tube and 12 ml of Listeria hybridization solution (6xSSC, 0.5%SDS, 1x Denhardts, 1 mM EDTA and 12 uCi of labeled Listeria probe) prewarmed to 65° C. added. The tube and contents were placed in a 65° C. water bath for 120 minutes.

After hybridization, the filters were washed as follows. The contents of the tube were discarded and 25 ml of Listeria wash solution (0.5xSSC, 0.1% SDS, 0.16% antifoam B), prewarmed to 65° C., was added. The tube was shaken and placed at 65° C. for 5 minutes. The tube was then again shaken and the liquid poured out. This process was repeated five more times.

The washed filters were removed from the tube and placed on a clean sheet of paper to count in a beta-counter for 30 seconds, and the cpm for each filter recorded.

Generally the average of 3 negative control filters (prepared from a selected non Listeria bacterium) was taken and 500 cpm added to this value. This number is defined as the cutoff value. Filters with more cpm are suspect for Listeria, those with less indicate the absence of Listeria.

Other embodiments are within the following claims.

We claim:

1. A nucleic acid fragment capable of hybridizing, under predetermined stringency conditions, to rRNA of Listeria monocytogenes and not to rRNA of *Bacillus subtilis*.

2. The nucleic acid fragment of claim 1 wherein said fragment is not capable of hybridizing, under said conditions, to rRNA of of 90% at least of the following microorganisms *Aeromonas sobria, Bacillus cereus, Bacillus subtilis, Brochothrix thermosphacta, Citrobacter freundii, Corynebacterium xerosis, Corynebacterium diptheriae, Escerichia vulneris, Enterobacter agglomerans, Enterobacter cloacae, Klebsiella pneumoniae, Klebsilla oxytoca, Lactobacillus casei, Pseudomonas aeruginosa, Rhodococcus eguii, Salmonella arizonae, Salmonella cholerae-suis, Salmonella typhi, Serratia odorifera, Shigella boydii, Shigella flexneri, Shigella sonnei, Staphylococcus aureus, Staphylococcus epidermidis, Staphylococcus hominis, Staphylococcus saprophyticus, Streptococcus agalacticae, Streptococcus bovis, Streptococcus faecalis, Streptococcus faecium, S-treptococcus lactis, Streptococcus mutans, Streptococcus pneumoniae, Streptomyces globisporus, Yersinia enterocolitica*.

3. The nucleic acid fragment of claim 1, said fragments being capable of hybridizing under hybridizing conditions to probe 568 or its complementary strand.

4. The nucleic acid fragment of claim 1, said fragments being capable of hybridizing under hybridizing conditions to probe 661 or its complementary strand.

5. The nucleic acid fragment of claim 1, said fragment being homologous with at least 75% of a 10 nucleotide or larger region of one of the five Listeria 16S rRNA regions shown in the Figure.

6. A method of detecting the presence of Listeria bacteria in a sample, comprising
contacting the nucleic acid fragment of claim 1 with bacteria in said sample under conditions that allow said fragment to hybridize to rRNA of said Listeria bacteria in said sample to form hybrid nucleic acid complexes, and
detecting said hybrid complexes as an indication of the presence of said Listeria bacteria in said sample.

7. The method of claim 8 comprising culturing bacteria in said sample under culture conditions which allow growth of Listeria but not of Brochothrix.

8. The method of claim 9 wherein said culture conditions is a growth temperature above 30° C.

9. A method for detecting Listeria in a sample comprising bacteria, said method comprising growing said bacteria at a temperature above 30° C., and then contacting, under hybridizing conditions, the rRNA of said bacteria with a nucleic acid probe able to hybridize to rRNA of *L. monocytogenes* and rRNA of Brochothrix but not to rRNA of *B. sublitis*, and detecting hybrid complexes as an indication of the presence of Listeria in said sample.

10. The method of claim 6 wherein, prior to said contacting, said sample is subjected to a primary enrichment step for Listeria, followed by a secondary, non-specific bacterial enrichment step, said secondary enrichment step being carried out in a buffer solution to maintain the pH of said enriched sample between 6.5 and 8.0.

11. The method of claim 10 wherein said pH is maintained at about 7.2.

12. The method of claim 6 wherein, prior to said contacting, Listeria in said sample are contacted with an enzyme to weaken their cell walls, and are then lysed.

13. The nucleic acid fragment of claim 1, wherein said fragments being capable of hybridizing under hybridizing conditions to probe 609 or its complementary strand.

* * * * *

UNITED STATES PATENT AND TRADEMARK OFFICE
CERTIFICATE OF CORRECTION

PATENT NO. : 5,089,386                         Page 1 of 2

DATED : February 18, 1992

INVENTOR(S) : Erko Stackebrandt, Michael Curiale

It is certified that error appears in the above-identified patent and that said Letters Patent is hereby corrected as shown below:

Column 4, line 32, "sequence" is misspelled;

Column 7, line 40, "accessibility" is misspelled;

Column 7, line 63, "equally" is misspelled;

Column 8, line 46, delete "vp" before "Na salt)";

Colum 8, line 56, after "10 x TE", insert the following: --(Tris-HCl 10 mM, EDTA, 1mM, pH 7.6)--;

Column 8, line 66, "liquid" is misspelled;

Column 9, line 2, "liquid" is misspelled;

Column 9, line 5, "liquid" is misspelled;

Column 9, claim 2, line 43, delete "of", second occurrence;

Column 10, claim 9, line 35, "subtilis" is misspelled.

UNITED STATES PATENT AND TRADEMARK OFFICE
CERTIFICATE OF CORRECTION

PATENT NO. : 5,089,386

DATED : February 18, 1992

INVENTOR(S) : Erko Stackerbrandt, Michael Curiale

It is certified that error appears in the above-identified patent and that said Letters Patent is hereby corrected as shown below:

Column 8, line 57, delete (-HcI mM, 7.6).

Signed and Sealed this

Tenth Day of August, 1993

Attest:

MICHAEL K. KIRK

Attesting Officer     Acting Commissioner of Patents and Trademarks